United States Patent [19]

Lütticken et al.

[11] Patent Number: 4,788,056

[45] Date of Patent: Nov. 29, 1988

[54] COMBINED VACCINE FOR VIRAL AND BACTERIAL INFECTIONS

[75] Inventors: Heinrich D. Lütticken; Nicolaas Visser, both of Boxmeer; Eric O. Rijke, Am Beugen, all of Netherlands

[73] Assignee: Akzo N.V., Arnhem, Netherlands

[21] Appl. No.: 36,408

[22] Filed: Apr. 9, 1987

[30] Foreign Application Priority Data

Apr. 21, 1986 [NL] Netherlands ........................ 8601001

[51] Int. Cl.⁴ .................... A61K 39/02; A61K 39/12; C12N 9/00; C12N 9/52
[52] U.S. Cl. ......................................... 424/89; 424/88; 424/90; 424/91; 424/92; 424/93; 530/407; 530/416; 530/417; 530/427; 435/183; 435/184; 435/219; 435/220
[58] Field of Search ..................................... 424/88–93; 530/407, 427, 416, 417; 435/183–184, 219, 220

[56] References Cited

U.S. PATENT DOCUMENTS

| 3,651,214 | 3/1972 | Raettig | 424/92 |
| 3,873,422 | 3/1975 | Mebus | 424/89 |
| 4,298,597 | 11/1981 | Acres et al. | 424/92 |
| 4,440,748 | 4/1984 | Graham | 424/92 |
| 4,650,677 | 3/1987 | Roerink | 424/89 |
| 4,657,761 | 4/1987 | Pinto | 424/92 |
| 4,680,176 | 7/1987 | Berns | 424/89 |

OTHER PUBLICATIONS

Fares et al. CA., vol 101,1983, #88526p.
Snodgrass et al., *Infection and Immunity*, vol. 37, No. 2, pp. 586–591, (1982).

*Primary Examiner*—Johnnie R. Brown
*Assistant Examiner*—Garnette D. Draper
*Attorney, Agent, or Firm*—William M. Blackstone

[57] ABSTRACT

Vaccines containing both *E.coli* and herpes virus were found not to provide adequate protection against subsequent herpes virus infections. The present invention is concerned with a *E.coli* herpes virus combined vaccine which provides protection against both types of pathogen.

11 Claims, No Drawings

COMBINED VACCINE FOR VIRAL AND BACTERIAL INFECTIONS

The invention relates to a combined vaccine and also to a method for the preparation of such a vaccine and to the use of such a vaccine.

In commercial stock-breeding the role of vaccination for the maintenance of a healthy livestock population is particularly important.

This applies in particular also to intensive stock-breeding with associated high population densities, where a viral, bacterial or parasitic infection can affect the whole stock in a short time—often with disastrous consequences.

To prevent infection livestock are therefore vaccinated, for example, separately against, inter alia, *Escherichia coli* (*E. coli*) infections, and against herpes virus infections, such as pseudorabies (also termed Aujeszky's disease).

Said vaccinations are usually carried out by administering immunogenic material in the form of live (attenuated or unattenuated) pathogens, or by means of killed pathogens.

It is obvious that from the economic point of view it is attractive to prepare immunogenic material from various pathogens combined as one vaccine and to administer it as such.

It was found not to be possible, however, to prepare a combined vaccine which has a stable immunizing activity both against disorders due to *E. coli* and against disorders due to herpes virus by simply adding fresh *E. coli* material and viral material together. Surprisingly, it has also been found, however, that such a combined vaccine can in fact be prepared.

The object of the present invention is therefore to provide a combined vaccine with which immunization can be carried out simultaneously against *E. coli* and against herpes virus.

More particularly, such a vaccine contains immunogenic *E. coli* material and viral material in which undesired enzyme activity is inhibited or is largely absent.

Surprisingly, it has been found in particular that the immunogenic activity of the viral material present in the combined vaccine is substantially improved if the enzyme activity is suppressed or removed prior to, during and/or after the combination of the two vaccine components.

Probably, this concerns in particular the activity of enzymes present in the *E. coli* material. Without being able to advance an explanation for this with certainty, the supposition is that, in particular, proteolytic enzymes from the *E. coli* material might adversely affect the immunogenic potency of the combined vaccine.

The *E. coli* material, and if desired also the virus material, can be rendered free or virtually free of enzyme activity prior to the preparation of the combined vaccine. This may be performed actively or passively.

The enzyme activity may be removed passively by storing the *E. coli* material for the preparation of the combined vaccine separate for at least a sufficiently long time. Sufficient is, for example, approximately two to four weeks at approximately 4° C. In the light of the possible explanation advanced above it could be concluded that as a result of this an ageing process occurs in which the proteolytic enzymes are inactivated. It is possible to actively render free from enzyme activity, for example, by first largely free the separate materials from enzyme activity, for example by precipitation, (column) chromatography, centrifuging, electrophoresis, or other biochemical or microbiological separation and purification methods or by adding enzyme inhibitors, by keeping the materials for a sufficiently long period, by adding high concentrations of foreign protein (for example in the form of serum or serum proteins), or by denaturing the enzymes.

As an alternative, or in addition, the enzyme activity can be markedly or completely reduced during or immediately after the preparation of the combined vaccine, for example, by adding enzyme inhibitors or high concentrations of foreign protein, or by separating the enzyme activity from the immunogenic materials by means of biochemical or microbiological separation methods.

The invention relates in particular to combined vaccines in which herpes viruses such as pseudorabies virus or bovine herpes virus are incorporated.

Suitable enzyme inhibitors are, for example: N-ethylmaleimide, monoiodoacetate, monoiodoacetamide, Trasylol, EDTA, PMSF and trypsin inhibitors such as the so-called "soybean trypsin inhibitor".

Suitable proteins for adding to the vaccine or the vaccine components are, for example, the serum proteins, already mentioned earlier, in the form of total serum or certain components thereof (such as, for example, the serum albumins) or milk proteins or egg proteins.

In the vaccines according to the invention the isolated antigen fraction of *E. coli* or *E. coli* variants (spontaneous or induced mutants, or *E. coli* modified by recombinant DNA techniques) is used. For pig vaccines this refers, for example, to an antigen fraction which contains the so-called K88-pili antigen. Of course, *E. coli* antigens may be used which have been prepared by a different microorganism, the genetic material of which has been modified by means of recombinant techniques in a manner such that *E. coli* antigens can be produced if desired with increased yield.

The herpes viral material for the vaccine according to the invention comprises killed or live, if desired attenuated, virus, the pathogenicity and/or the virulence of which is reduced or destroyed optionally by spontaneous or induced mutations or by recombinant DNA techniques. And it is optionally also possible to use isolated immunogenic viral material in the combined vaccine.

It is found to be possible, for example, to use such a combined vaccine according to the invention for the simultaneous immunization of pigs to protect their offspring both against pig diarrhoea and against pseudorabies viral infections.

A vaccine according to the invention may, if desired, contain the following components in addition to the immunogenic material:

stabilizers;

adjuvants, such as aluminium salts (for example Al(OH)$_3$; AlPO$_4$, Al$_2$(SO$_4$)$_3$); Ca$_3$(PO$_4$)$_2$; saponin; DDA; Pluronics; avridin; oil-in-water emulsions, if desired together with vitamin E, Pluronics, avridin, dextran sulphate or the like: water-in-oil emulsions, if desired with Marcol, Polysorbate 80, polysorbitan monooleate, saponin, miglyol, isopropyl myristate, isopropyl palmitate or the like, or in the form of capsules of, for example, gelatin or hydroxypropylmethylcellulose phthalate with or without saponin;

buffers such as phosphate buffer, bicarbonate buffer or tris buffer, preferably in a strength of 5–100 mmol/l;

preservatives such as Thiomersal, m- or o-cresol or formalin (preferably in a quantity of 0.2-0.5%) or benzyl alcohol (preferably 1-2%).

The invention is explained by reference to the following examples.

EXAMPLE 1

In order to establish the negative effects of untreated *E. coli* antigens on pseudorabies virus, the infectivity of the pseudorabies virus was measured in the presence of an equal volume of the *E. coli* antigens.

*E. coli* antigens were prepared as follows. *E. coli*'s were cultured in casein hydrolysate/sorbitol media under standard conditions with continuous adjustment of pH, oxygen and stirring intensity in a fermentator.

After 40 hours the culture was stopped and the content of the fermentator was heated for 15 minutes at 60°–65° C. After cooling down the material was centrifuged. The antigens in the supernatant were concentrated by ultrafiltration. The resulting antigen concentrate was incubated for 16 hours at 37° C. in the presence of 0.5% formaline.

After incubating the freshly prepared *E. coli* antigen with pseudorabies virus for 1 hour at 37° C., the virus was titered out in 10-fold dilutions into microtiter plates on monolayers of Vero cells. The virus titer was calculated from the CPEs found.

The results in Table I show that the *E. coli* material has an appreciable effect on the infectivity of the pseudorabies virus.

TABLE I

| No. | Pseudorabies virus (ml) | *E. coli* antigens ml | *E. coli* antigens type | Titer ($log^{10}$/ml) | ΔTiter compared with control |
|---|---|---|---|---|---|
| 1 | 0.5 | — | — | 5.27 | — |
| 2 | 0.5 | 0.5 | K88ab | 3.05 | 2.22 |
| 3 | 0.5 | 0.5 | K88ac | 2.53 | 2.74 |
| 4 | 0.5 | 0.5 | K99 | 4.79 | 0.48 |

EXAMPLE 2

Effect of the *E. coli*-pseudorabies combination on the pseudorabies protection test with and without (pre)treatment of the *E. coli* antigens This example demonstrates that without the treatments according to the invention, the combination of pseudorabies antigen and *E. coli* antigens does not result in an efficient vaccine combination. The effectiveness of the pseudorabies antigens was measured in a mouse protection test.

The mice (C57 b110 strain) were vaccinated with a decreasing quantity of vaccine (100, 25 or 6.25 μl respectively) and after 4 weeks a test infection was carried out with the virulent pseudorabies virus strain, Phylaxia. From this the dose was calculated which gives 50% protection ($PD_{50}$). From the experiments it is evident that without treatment of the *E. coli* antigen the vaccine does not satisfy the quality requirements for pseudorabies vaccine ($PD_{50} \leqq 50$ μl).

After treatment according to the invention the combined vaccine does in fact satisfy said quality requirement.

TABLE II

| Batch No. | Pseudorabies antigen | *E. coli* LTK88 | Treatment | $PD_{50}$ (in μl) | Notes |
|---|---|---|---|---|---|
| 3592 | 40% | 5% | none | >150 | rejected (≧50) |
| 3633 | 40% | — | none | 25.0 | good |
| 4508 | 41% | 4% | none | 119.0 | rejected (≧50) |
| 4509 | 41% | — | 10% calf serum | 10.7 | good (≦50) |
| 4510 | 41% | 4% | 10% calf serum | 28.0 | good (≦50) |
| 5087 | 25% | — | none | 12.9 | good (≦50) |
| 5089 | 25% | 12% | 4% calf serum | 40.7 | good (≦50) |
| 5091 | 25% | 12% | 200 units of trasylol | 19.1 | good (≦50) |

EXAMPLE 3

Use of enzyme inhibitors in *E. coli*-pseudorabies combined vaccine

The presumed endogenous protease activities were suppressed by means of a number of enzyme inhibitors. The choice given does not exclude other inhibitors.

The effect of the inhibitors were measured in a standard ELISA for determining antigen quantities.

Without treatment the measurable quantity of pseudorabies antigen is reduced to 53%. As a result of the various treatments at least 93% of the antigen quantity remains measurable in this test.

TABLE III

| No. | pseudorabies antigen | *E. coli* antigens | Treatment | ELISA result compared with control (N) |
|---|---|---|---|---|
| 1 | + | — | — | 101.0% (5) |
| 2 | — | + | — | 0% (3) |
| 3 | + | + | — | 53.0% (3) |
| 4 | + | + | PMSF | 92.9% (5) |
| 5 | + | + | NMI | 102.9% (4) |
| 6 | + | + | MIA | 93.9% (3) |
| 7 | + | + | TRAS | 94.5% (3) |
| 8 | + | + | TI | 97.5% (4) |
| 9 | + | + | EDTA | 95.3% (3) |
| 10 | + | + | ageing | 102.5% (10) |

PMSF: phenylmethanesulphonyl fluoride
NMI: N—ethylmaleimide
MIA: monoiodoacetamide
TI: trypsin inhibitor (soybean)
TRAS: Trasylol
EDTA: ethylenediamine tetraacetic acid.

EXAMPLE 4

Treatment of the *E. coli* antigens according to the invention ("Ageing")

6–8-week-old mice (Swiss albino) were intramuscularly injected with graded dosages (4, 16 or 64 μl respectively) of the specified vaccines. Four weeks after vaccination the mice were given a test infection as in Example 2.

The protection of the mice is expressed in the dose which gives 50% protection ($PD_{50}$). The quality requirement for approval is that the $PD_{50}$ should be ≦50 μl.

The antibodies for the *E. coli* components were measured in the sera of the same mice by means of a standard ELISA for the determination of antibody titers. Each figure is the average of 6 sera.

Conclusions:

The antibody titers for the *E. coli* components are comparable in the combined vaccine with those of the *E. coli* vaccine on its own. The protection test against pseudorabies in mice satisfies the quality requirements for such a combined vaccine.

TABLE IV

| Batch No. | Pseudorabies antigen | E. coli antigen | PD$_{50}$ | Anti E. coli titers (16 μl dose) log$_2$ in ELISA | | | | |
|---|---|---|---|---|---|---|---|---|
| | | | | LT | K88ab | K88ac | K99 | 987P |
| 6704 | + | | 5.4 | | | | | |
| 6705 | + | | 11.9 | | | | | |
| 6706 | + | | 19.5 | | | | | |
| 6707 | | + | | 6.8 | 10.8 | 10.8 | 8.2 | 11.2 |
| 6708 | | + | | 6.5 | 10.8 | 10.2 | 8.8 | 11.5 |
| 6709 | | + | | 7.3 | 11.7 | 12.3 | 10.0 | 11.7 |
| 6710 | + | + | 16.1 | 6.8 | 12.5 | 12.3 | 9.0 | 12.5 |
| 6711 | + | + | 8.9 | 7.5 | 12.2 | 12.2 | 9.5 | 12.2 |
| 6712 | + | + | 23.6 | 7.2 | 11.8 | 11.7 | 9.0 | 12.2 |

We claim:

1. Combined live-stock vaccine, comprising an effective amount of a combination of at least one type of immunogenic material of *E. coli*, selected from pili, pili proteins and *E. coli* antigens, and immunogenic viral material of pseudorabies virus or pseudorabies antigen in a pharmaceutically acceptable carrier.

2. Combined vaccine according to claim 1, characterized in that it is essentially free of undesired *E. coli* enzyme activity.

3. Combined vaccine according to claim 1, characterized in that at least a portion of the viral material is pseudorabies virus or material with the immunogenic properties of pseudorabies virus.

4. Combined live-stock vaccine, comprising an effective amount of a combination of at least one type of immunogenic material of *E. coli*, selected from pili, pili proteins, and *E. coli* antigens, and immunogenic material of bovine herpes virus or bovine herpes virus antigens in a pharmaceutically acceptable carrier.

5. Method for the immunization of live-stock, characterized in that a combined vaccine according to claim 1 is administered in an immunogenically adequate quantity.

6. Method for preparation of vaccine composition according to claim 1, comprising combining immunogenically effective amounts of active immunogenic material of *E. coli* and immunogenic viral material of pseudorabies virus and a pharmaceutically acceptable carrier, wherein at least the *E. coli* material is rendered essentially free of enzyme activity by at least one method selected from the group consisting of:
   a. storing the *E. coli* material separately for a sufficiently long time for any proteolytic enzymes contained therein to become inactivated;
   b. separating any proteolytic enzymes contained in the *E. coli* material from said material by differences in molecular size, electrical charge or bonding characteristics;
   c. adding enzyme inhibitors;
   d. denaturing the enzymes; and
   e. adding protein material.

7. Method according to claim 6, wherein the composition is rendered essentially free of enzyme activity by adding at least one enzyme inhibitor selected from the group consisting of N-ethylmaleimide, monoiodoacetate, monoiodoacetamide, Trasylol, ethylenediamine tetraacetic acid, phenylmethanesulphonyl fluoride and trypsin inhibitors.

8. Method according to claim 6, characterized in that at least one common component for the preparation of vaccines selected from the group consisting of:
   a. stabilizers;
   b. adjuvants;
   c. buffering substances; and
   d. preservatives, is added to the vaccine composition.

9. Method according to claim 6, wherein the *E. coli* material is rendered essentially free of enzyme activity prior to being combined with the viral material.

10. Method according to claim 6, wherein the *E. coli* material is rendered essentially free of enzyme activity before being combined with the viral material.

11. Method according to claim 6, wherein the *E. coli* material is rendered essentially free of enzyme activity after being combined with the viral material.

* * * * *